United States Patent
Wodecki

(10) Patent No.: US 9,980,703 B2
(45) Date of Patent: May 29, 2018

(54) METHODS AND SYSTEMS FOR A DISPLAY INTERFACE FOR DIAGNOSTIC MEDICAL IMAGING

(71) Applicant: General Electric Company, Schenectady, NY (US)

(72) Inventor: Lionel Wodecki, Buc (FR)

(73) Assignee: General Electric Company, Schenectady, NY (US)

( * ) Notice: Subject to any disclaimer, the term of this patent is extended or adjusted under 35 U.S.C. 154(b) by 552 days.

(21) Appl. No.: 14/659,752

(22) Filed: Mar. 17, 2015

(65) Prior Publication Data
US 2016/0270764 A1    Sep. 22, 2016

(51) Int. Cl.
*A61B 8/00*    (2006.01)

(52) U.S. Cl.
CPC ............ *A61B 8/462* (2013.01); *A61B 8/4405* (2013.01); *A61B 8/4427* (2013.01); *A61B 8/465* (2013.01); *A61B 8/467* (2013.01); *A61B 8/54* (2013.01)

(58) Field of Classification Search
CPC ..... A61B 8/4405; A61B 8/4427; A61B 8/462; A61B 8/465; A61B 8/467; A61B 8/54
See application file for complete search history.

(56) References Cited

U.S. PATENT DOCUMENTS 6,716,167 B1 *  4/2004  Henderson ............... A61B 8/00
                                                           600/437
2007/0276287 A1   11/2007  Donaldson et al.
2009/0198135 A1 *  8/2009  Yanagihara ............... A61B 8/14
                                                           600/443
2009/0292163 A1 *  11/2009  Kassab ................. A61B 17/122
                                                           600/104
2013/0005443 A1 *  1/2013  Kosta .................. G07F 17/3206
                                                           463/25

(Continued)

FOREIGN PATENT DOCUMENTS

WO    2001053919 A2    7/2001
WO    2014148688 A1    9/2014

OTHER PUBLICATIONS

International Search Report and Written Opinion for corresponding PCT application No. PCT/US2016/019832 dated May 31, 2016; 13 pages.

*Primary Examiner* — Mark Remaly
(74) *Attorney, Agent, or Firm* — Dean D. Small; The Small Patent Law Group, LLC

(57) ABSTRACT

An ultrasound imaging system and method is provided that includes an ultrasound probe configured to acquire ultrasound data for a region of interest and a controller circuit communicatively coupled to the ultrasound probe configured to generate one or more ultrasound images from the ultrasound data. The ultrasound imaging system and method further provide a curved housing shaped to extend along a curvature angle, the curved housing includes a front panel having a curved touchscreen having at least a first interface section, a second interface section, and a third interface section formed integral with one another. The first interface section and the third interface section are positioned at different display angles with respect to each other. The first interface section is also configured to display one or more ultrasound images, and the third interface section includes one or more user selectable icons to control the ultrasound probe.

20 Claims, 11 Drawing Sheets

(56) References Cited

U.S. PATENT DOCUMENTS

| | | |
|---|---|---|
| 2014/0066766 A1 | 3/2014 | Stonefield et al. |
| 2014/0088428 A1 | 3/2014 | Yang et al. |
| 2014/0361251 A1* | 12/2014 | Krall ........................ H01L 51/52 257/40 |
| 2015/0002490 A1 | 1/2015 | Han et al. |
| 2015/0342562 A1* | 12/2015 | Messina ................. A61B 8/462 248/544 |

* cited by examiner

METHODS AND SYSTEMS FOR A DISPLAY INTERFACE FOR DIAGNOSTIC MEDICAL IMAGING

BACKGROUND OF THE INVENTION

Embodiments described herein generally relate to display interfaces for diagnostic medical imaging, and more particularly to a display interface for an ultrasound system.

Diagnostic medical imaging systems typically include a scan portion and a control portion having a display. For example, ultrasound imaging systems usually include ultrasound scanning devices, such as ultrasound probes having transducers that are connected to an ultrasound system to control the acquisition of ultrasound data by performing various ultrasound scans (e.g., imaging the volume or body).

Settings and/or configurations of the ultrasound system is controlled by a clinician using a user interface 110. FIG. 1 illustrates a perspective view of a conventional ultrasound system 100. In the conventional ultrasound systems 100, the user interface 110 is divided into three distinct elements a flat screen or display 104, a separate touchscreen 106, and an operating panel 108 conventionally mounted to a cart 102. For example, the flat screen 104 displays one or more ultrasound images acquired by the ultrasound system 100. Additionally, the flat screen 104 may include a graphical user interface (GUI) that is used in connection with the operating panel 108. The touchscreen 106 is used by the user or clinician to configure or adjust settings of one or more ultrasound scanning devices. The operating panel 108 includes physical buttons and a trackball used to interface with the GUI of the flat screen display 104.

However, by having separate elements for the user interface 110 the size and weight of the conventional ultrasound system 100 is increased hindering the portability of the conventional ultrasound system. Additionally, for example, the size attributed to the user interface elements limits the ability for clinicians to adjust and/or customize relative positions of the elements. Further, separate user interface elements increase the amount of surface area needed to clean and/or sterilize the user interface. For these and other reasons, an improved display interface is needed for diagnostic medical imaging.

BRIEF DESCRIPTION OF THE INVENTION

In one embodiment, an ultrasound imaging system is provided that includes an ultrasound probe configured to acquire ultrasound data for a region of interest and a controller circuit communicatively coupled to the ultrasound probe configured to generate one or more ultrasound images from the ultrasound data. The system further provides a curved housing shaped to extend along a curvature angle. The curved housing includes a front panel having a curved touchscreen having at least a first interface section, a second interface section, and a third interface section formed integral with one another. The first interface section and the third interface section are positioned at different display angles with respect to each other. The first interface section is also configured to display one or more ultrasound images, and the third interface section includes one or more user selectable icons to control the ultrasound probe.

In another embodiment, a portable ultrasound imaging system is provided that includes an ultrasound probe configured to acquire ultrasound data for a region of interest and a controller circuit communicatively coupled to the ultrasound probe configured to generate one or more ultrasound images from the ultrasound data. The system further includes a movable cart having a plurality of wheels. The portable ultrasound imaging system also includes a curved housing shaped to extend along a curvature angle. The curved housing includes a front panel having a curved touchscreen having at least a first interface section, a second interface section, and a third interface section formed integral with one another. The first interface section and the third interface section are positioned at different display angles with respect to each other. The first interface section is also configured to display one or more ultrasound images, and the third interface section includes one or more user selectable icons to control the ultrasound probe. The portable ultrasound imaging system also includes an arm mount coupled to the curved touchscreen and the movable cart. The arm mount is configured to adjust a vertical position and a rotational position of the curved touchscreen with respect to the movable cart.

In another embodiment, an ultrasound imaging system is provided that includes an ultrasound probe configured to acquire ultrasound data for a region of interest and a controller circuit communicatively coupled to the ultrasound probe configured to generate one or more ultrasound images from the ultrasound data. The system also includes an examination chair having a support rail positioned around the head portion of the examination chair. The ultrasound imaging system also includes a curved housing shaped to extend along a curvature angle. The curved housing includes a front panel having a curved touchscreen having at least a first interface section, a second interface section, and a third interface section formed integral with one another. The first interface section and the third interface section are positioned at different display angles with respect to each other. The first interface section is also configured to display one or more ultrasound images, and the third interface section includes one or more user selectable icons to control the ultrasound probe. The ultrasound imaging system also includes an arm mount coupled to the curved touchscreen and the support rail of the examination chair. The arm mount is traversable along the support rail.

DETAILED DESCRIPTION OF THE INVENTION

Figure 1:
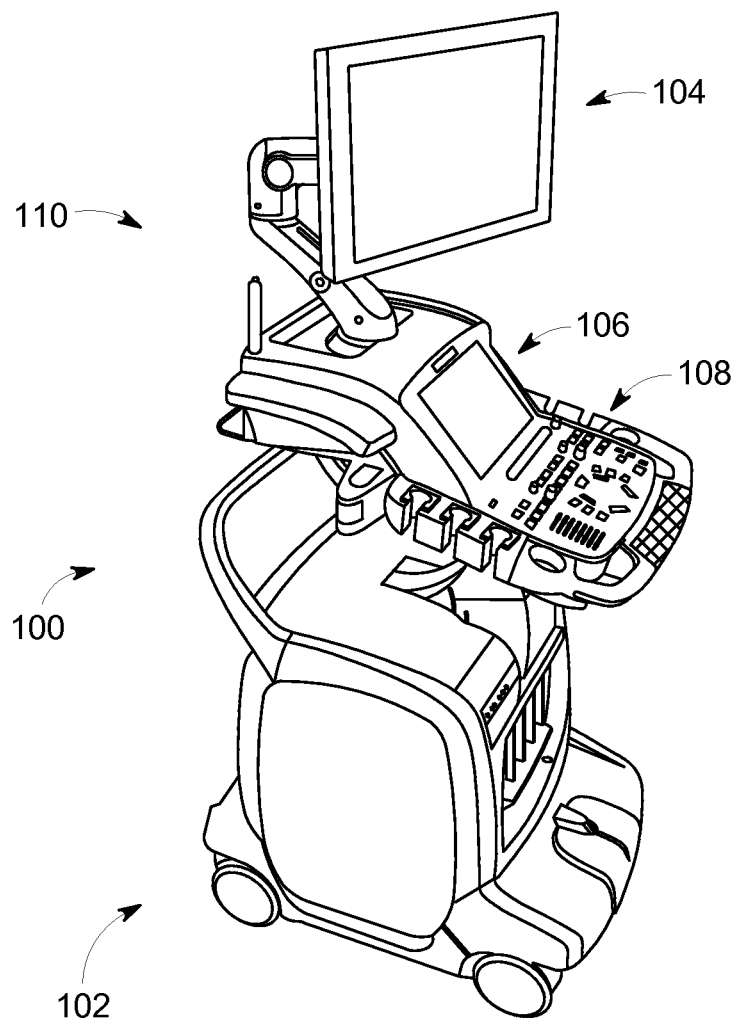
FIG. 1 illustrates a perspective view of a conventional ultrasound system.

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for display interfaces for diagnostic medical imaging, and more particularly to ultrasound imaging systems using a curved touchscreen. The curved touchscreen combines user interface elements corresponding to a flat screen for viewing ultrasound images, an operating panel, and graphical user interface. The curved touchscreen further allows a digital height adjustment of the image with an eye tracking module. The eye tracking module may include an image acquisition unit such as a camera (e.g., a digital camera), an image sensor (e.g., a charge-coupled device (CCD) image sensor, a complementary metal-oxide-semiconductor sensor, active pixel sensor, analog image sensor, a backside illumination sensor), or the like. The eye tracking module may be configured to optimize a position of one or more graphical user interfaces displayed on the curved touchscreen for a vertical position of the user or an eye height of the user.

Additionally or alternatively, the curved touchscreen may further be coupled to an arm mount. The arm mount is configured to adjust a vertical position and a rotational position (e.g., swivel) of the curved touchscreen. Optionally, the arm mount may include a first trigger and a second trigger. For example, the curved touchscreen may be adjusted in the vertical position when the first trigger is activated. In another example, the curved touchscreen may be adjusted in the rotational position (e.g., swivel) when the second trigger is activated.

Additionally or alternatively, the curvature of the curved touchscreen, such as a curvature angle, may be adjusted to avoid light reflection on the surface. For example, the curved touchscreen may be flexible allowing a user (e.g., clinician, echographer, doctor, nurse) to reduce and/or increase the curvature angle of the curved touchscreen.

A technical effect of at least one embodiment includes improved ability to sterilize and/or clean the user interface. A technical effect of at least one embodiment includes better user position during review of acquired and/or previously acquired ultrasound images. A technical effect of at least one embodiment includes reduction in the size, weight, and/or number of parts comparable to conventional ultrasound imaging systems. A technical effect of at least one embodiment includes increased mobility relative to conventional ultrasound imaging systems. A technical effect of at least one embodiment includes allowing a user to perform multiple ultrasound examinations corresponding to multiple patient positions within one ultrasound imaging system.

Figure 2:
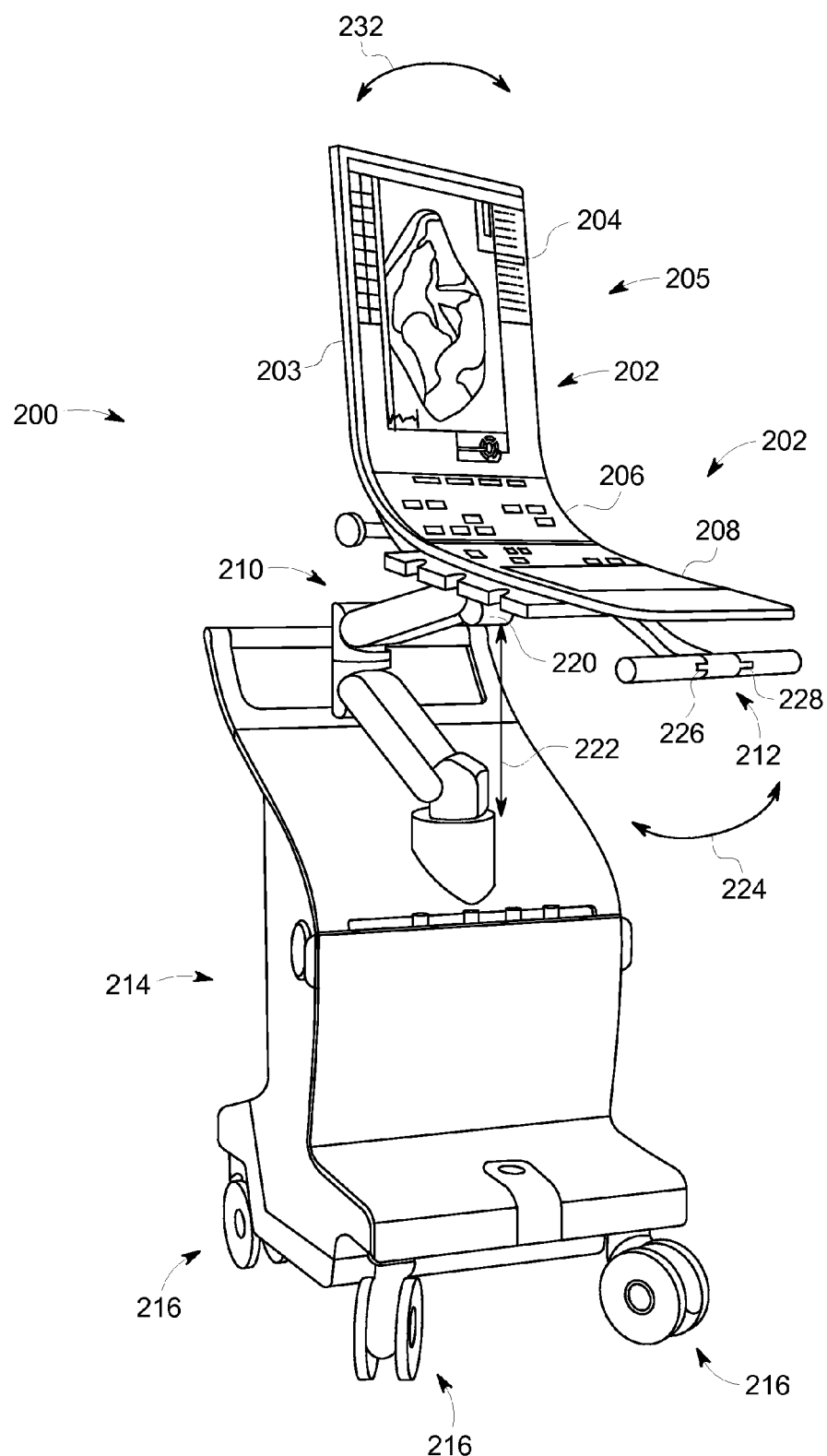
FIG. 2 illustrates a perspective view of an ultrasound imaging system, in accordance with an embodiment.

FIG. 2 illustrates a perspective view of an ultrasound imaging system 200 in accordance with various embodiments described herein. The ultrasound imaging system 200 includes a curved housing 203 that extends along a non-zero, non-orthogonal curvature angle. The curved housing 203 includes a front panel 205 having a curved touchscreen 202. The curved touchscreen 202 includes at least a first interface section 204, a second interface section 206, and a third interface section 208 that are formed integral with one another. For example, the first interface section 204, the second interface section 206, and the third interface section 208 are molded integral with one another to enable enclosure within the curved housing 203 on a curved touchscreen 202.

Figure 3:
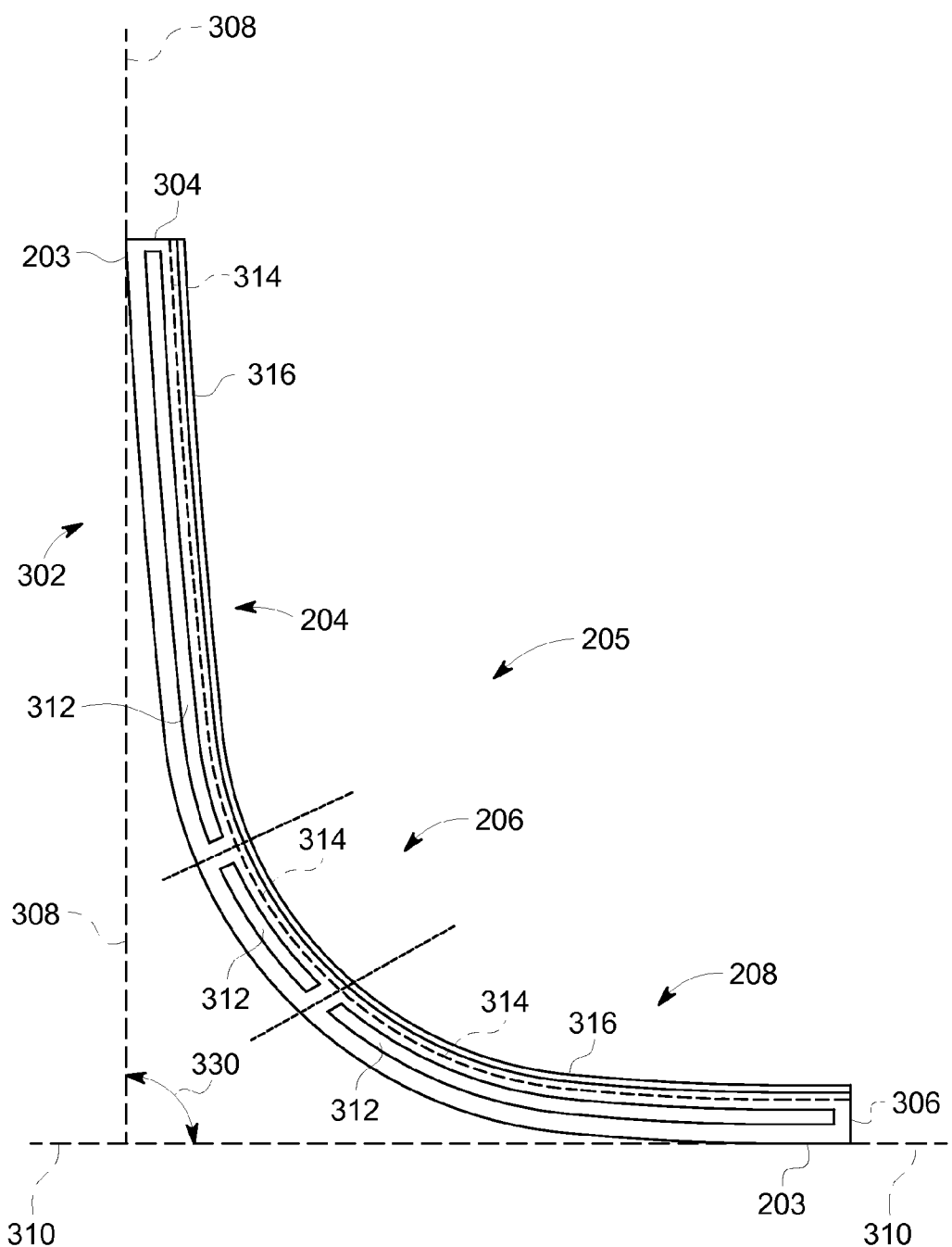
FIG. 3 illustrates a lateral schematic view of the curved housing of the ultrasound imaging system shown in FIG. 2, in accordance with an embodiment.

FIG. 3 illustrates a schematic view of the curved housing 203, in accordance with various embodiments described herein. The curved housing 203 includes a back surface 302, an upper end 304, a lower end 306, and the front panel 205. The curved housing 302 forms and extends along a curvature angle 330 based on the upper end 304 relative to the lower end 306. For example, the upper end 304 extends and/or is parallel to a longitudinal plane 308. The lower end 306 extends and/or is parallel to a latitude plane 310. The curvature angle 330, formed with respect to the longitudinal plane 308 and the latitude claim 310, may represent an obtuse angle.

In at least one embodiment, the curved housing 203 may be configured to be flexible allowing a user to adjust a position of the upper end 304 and/or the lower end 306 thereby adjusting the curvature angle 330 of the curved housing 203. For example, a user may reduce the curvature angle 330 by pulling and/or applying force to the back surface 302 proximate to either or both of the upper end 304 and/or the lower end 306 pivoting at or about the second interface section 206. In another example, the user may increase the curvature angle 330 by pushing and/or applying force to the front panel 205 proximate to either or both of the upper and 304 and/or the lower end 306 pivoting at or about the second interface section 206.

The front panel 205 includes the curved touchscreen 202. The curved touchscreen 202 may comprise one or more displays 312, one or more sensor substrates 314, and one or more cover glasses 316. The display 312 may be a liquid crystal display (e.g., light emitting diode (LED) backlight), an organic light emitting diode (OLED) display, or the like. Each display 312 of the curved touchscreen 202 shown in FIG. 3 corresponds to one of the interface sections (e.g., the first interface section 204, the second interface section 206, the third interface section 208). It should be noted that although multiple displays 312 are shown, in various other embodiments the curved touchscreen 202 may have a single display 312, two displays 312, and/or the like. For example, a single display 312 may correspond to the first interface section 204, the second interface section 206, and the third interface section 208. In another example, a single display 312 may correspond to two interface sections (e.g., the first interface section 204 and the second interface section 206, the second interface section 206 and the third interface section 208) and a second display 312 may correspond to a single interface section (e.g., the first interface section 204, the third interface section 208).

The cover glass 316 may be comprised of a transparent plastic, sapphire glass, silica, and/or the like. In various embodiments, the curved touchscreen 202 may have a cover-glass 316 that provides a continuous glass surface area (e.g., no cracks or sealing lines between and/or within the interface sections 204-208). For example, the cover glass 316 provides a single surface area that is overlaid over each of the interface sections 204-208 along the front panel 205. Additionally or alternatively, the curved touchscreen 202 may have more than one cover class 316 overlaid along the front panel 205. For example, a first cover glass may correspond to the first interface section 204, and a second cover glass may correspond to the third interface section 208. The sensor substrate 314 may be comprised of a transparent and/or optically transparent conducting surface, such as indium tin oxide (ITO), a metal mesh (e.g., a silver nano-tube mesh, a carbon mesh, graphene mesh), and/or the like. The sensor substrate 314 may be configured as an array of electrically distinct rows and columns of electrodes that extend through the first interface section 204, the second interface section 206, and the third interface section 208. Additionally or alternatively, the curved touchscreen 202 may have more than one sensor substrate 314 corresponding to a single interface section or two interface sections. For example, a first sensor substrate may extend through the first interface section 204, and a second sensor substrate may extend through the third interface section 208. In another example, a first sensor substrate may extend through the first and second interface sections 204, 206, and a second sensor substrate may extend through the third interface section 208.

Figure 9:
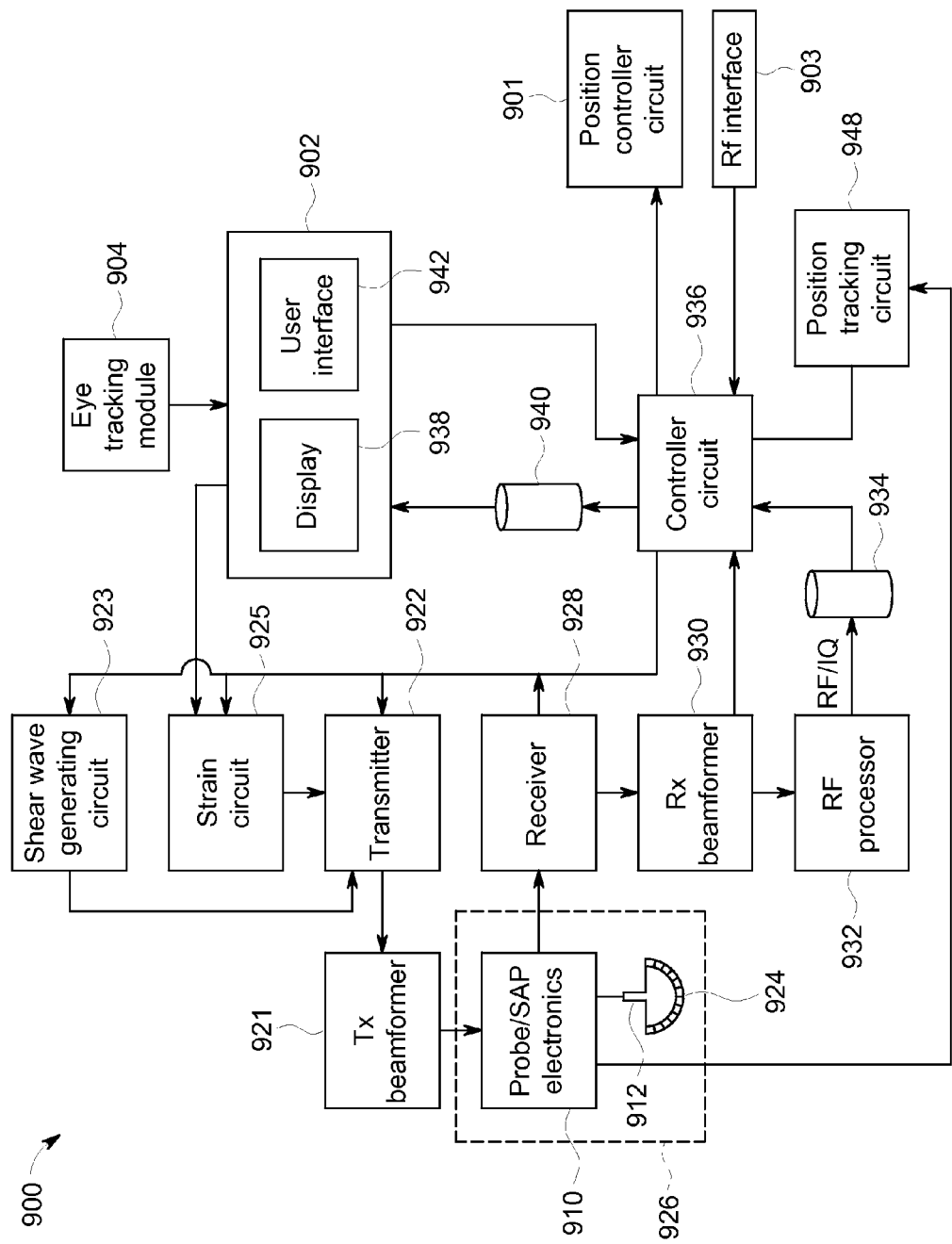
FIG. 9 is an illustration of a simplified block diagram of an ultrasound imaging system, in accordance with an embodiment.

The sensor substrate 314 may be coupled to a touchscreen controller circuit (not shown). A touchscreen controller circuit may include hardware, such as a processor, a controller, or other logic-based devices and/or a combination of hardware and software which is used to determine a position on the curved touchscreen controller activated and/or contacted by the user (e.g., finger(s) in contact with the cover glass 316 of the curved touchscreen 202). In various embodiments, the touchscreen controller circuit may be a part of and/or integrated with the controller circuit 936 (FIG. 9). The touchscreen controller may determine the position activated and/or contracted by the user by measuring a capacitance for each electrode (e.g., self-capacitance). For example, the touchscreen controller may transmit a current drive signal along a single electrode and measure a capacitance along the single electrode. Additionally or alternatively, the touchscreen controller may measure a capacitance for each intersection of a row and column electrode (e.g., mutual capacitance). For example, the touchscreen controller may transmit a current drive signal along a first electrode (e.g., a row electrode, a column electrode) and measure a mutual capacitance from a second electrode (e.g., a column electrode, a row electrode).

Based on the measured capacitance, the touchscreen controller may determine whether a finger(s) from the user is in contact and/or proximate to the sensor substrate 314. For example, when the capacitance, of the single electrode or intersection, is above a predetermined threshold the touchscreen controller may determine that the user is activating the corresponding single electrode or intersection. In another example, when the capacitance is below a predetermine threshold the touchscreen controller may determine that the single electrode or intersection is not activated.

Returning to FIG. 2, the curved housing 203 may be coupled and/or mounted to an arm mount 210. The arm mount 210 may be configured to adjust a vertical position, such as along a vertical arrow 222, and a rotational position (e.g., rotation centered about a pivot point 220), such as along a rotational arrow 224, of the curved touchscreen 202. Additionally or alternatively, a tilt angle of the curved touchscreen 202, along a tilt arrow 232, may be adjusted using the pivot point 220 of the arm mount 202.

Optionally, the arm mount 210 may be coupled with a position handle 212 that may include a first trigger 226 and a second trigger 228. Optionally, the first and second triggers 226 and 228 may include a tactile button, a rotational lock, or the like. Each trigger 226 and 228, when activated (e.g., compressing the tactile button, rotating the trigger), may allow directional movement (e.g., along the vertical arrow 222, along the rotational arrow 224) of the curved touchscreen 202 enabled by the arm mount 210. In at least one embodiment, the position handle 212 may be used by the user to adjust a position of the curved touchscreen 202. For example, the user may adjust the vertical position of the curved touchscreen 202 when the first trigger 226 is activated. In another example the user may adjust the rotational position of the curved touchscreen 202 when the second trigger 228 is activated.

In various embodiments, the first interface section 204 and the third interface section 208 are adjustable to be positioned at different display angles with respect to each other. For example, the first interface section 204 and the third interface section 208 may be positioned to form a right angle with respect to each other. In another example, the first interface section 204 and the third interface section 208 may be positioned to form an obtuse angle with respect to each other. It should be noted in various other embodiments that the second interface section 206 may be adjusted to be positioned at a different display angle with respect to the display angles of the first and third interface sections 204, 208. Optionally, the second interface section 206 may have approximately the same display angle with either the first interface section 204 or the third interface section 208.

Figure 4A:
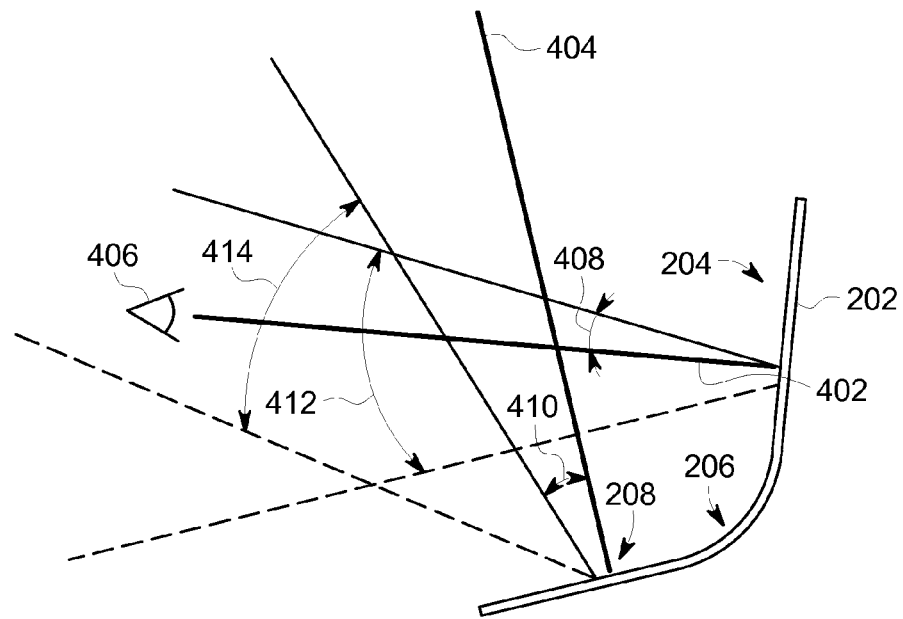
FIG. 4A illustrates a lateral view of a curved touchscreen of the ultrasound imaging system shown in FIG. 2, in accordance with an embodiment.
Figure 4B:
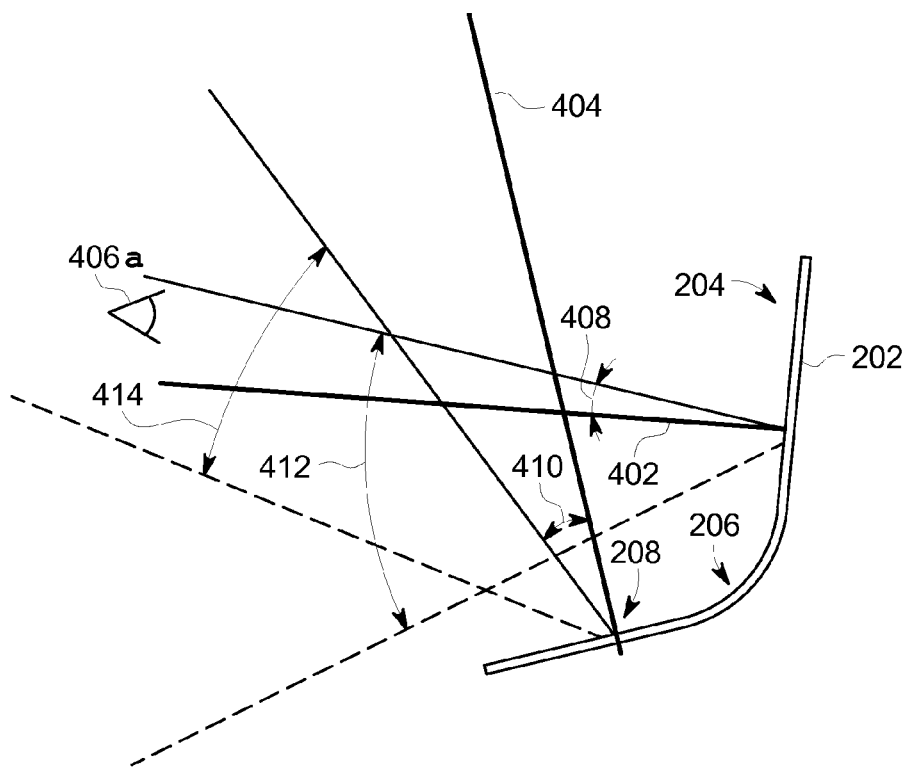
FIG. 4B illustrates the lateral view of the curved touchscreen of FIG. 4A at a different eye position, in accordance with an embodiment.

FIGS. 4A and 4B illustrate lateral views of the curved touchscreen 202. In connection with FIG. 4A, the display angle may be defined as a normal unit vector 402, 404 that extends perpendicular from the surface of the first and third interface sections 204 and 208, respectively. For example, the first interface section 204 has a first display angle corresponding to the normal unit vector 402, and the third interface 208 has a second display angle corresponding to the normal unit vector 404. Each of the normal unit vectors 402 and 404 correspond to and extend in different directions with respect to the user.

Additionally or alternatively, the display angle may be defined based on biasing angles 408 and 410 and/or viewing angles 412 and 414 which are based on the biasing angles 408 and 410, respectively. The biasing angles 408 and 410 may be a characteristic of the curved touchscreen 202 and are offset from the normal unit vectors 402 and 404 respectively. For example, the biasing angle 408 is offset for a top view (e.g., "12:00") or above the normal unit vector 402. In another example, the biasing angle 410 is offset for a bottom view (e.g., "6:00") or below the normal unit vector 404. The biasing angles 408 and 410 correspond to a visual direction in which the first interface section 204 and the third interface section 208, respectively, have a higher contrast ratio, a higher luminosity, a higher clarity, or the like with respect to other visual directions. For example, the eye(s) 406 is positioned such that the eye(s) 406 has a visual direction aligned with the normal unit vector 402. The eye(s) 406a, as shown in FIG. 4B, is positioned higher to the normal unit vector 402 relative to the eye(s) 406 as shown in FIG. 4A. The higher position of the eye(s) 406a is such that the eye(s) 406a has a visual direction aligned with the biasing angle 408 and will thereby have a higher contrast ratio, a higher luminosity, a higher clarity, and/or the like relative to the eye(s) 406 as positioned in FIG. 4A.

The viewing angles 412 and 414 correspond to a degree or positions of the user, particularly the eye(s) 406 of the user, away from the biasing angles 408 and 410 at which the first and third interface sections 204 and 208 can be viewed without noticeable degradation (e.g., when a contrast ratio decreases below a certain threshold, for example 2:1, 5:1, 10:1, or when a luminance is below a certain threshold, for example half of the maximum luminance). For example, the eye(s) 406 shown in FIG. 4 within the viewing angles 412 and 414 may be able to view the first and third interface sections 204 and 208 without noticeable degradation. In another example, an eye(s) of the user having a viewing direction within the viewing angle 414 but not within the viewing angle 412 may be able to view the third interface section 208 without noticeable degradation, but may view the first interface section 204 with noticeable degradation.

Returning to FIG. 2, the curved touchscreen 202 may be coupled to a movable cart 214. The movable cart 214 may include a plurality of wheels 216 enabling the movable cart 214 and the curved touchscreen 202 to be mobile. For example, the movable cart 214 may change positions or locations within a room, be moved to an alternative room or building relative to a present location of the movable cart 214, and the like. Additionally or alternatively, the curved touchscreen 202 may be coupled to a stationary cart. The stationary cart may be similar to the movable cart 214, however, the stationary cart may be in a static position within a room. For example, the stationary cart may be mounted to a wall of the room, mounted to a bed of the patient, and/or the like.

Figure 5:
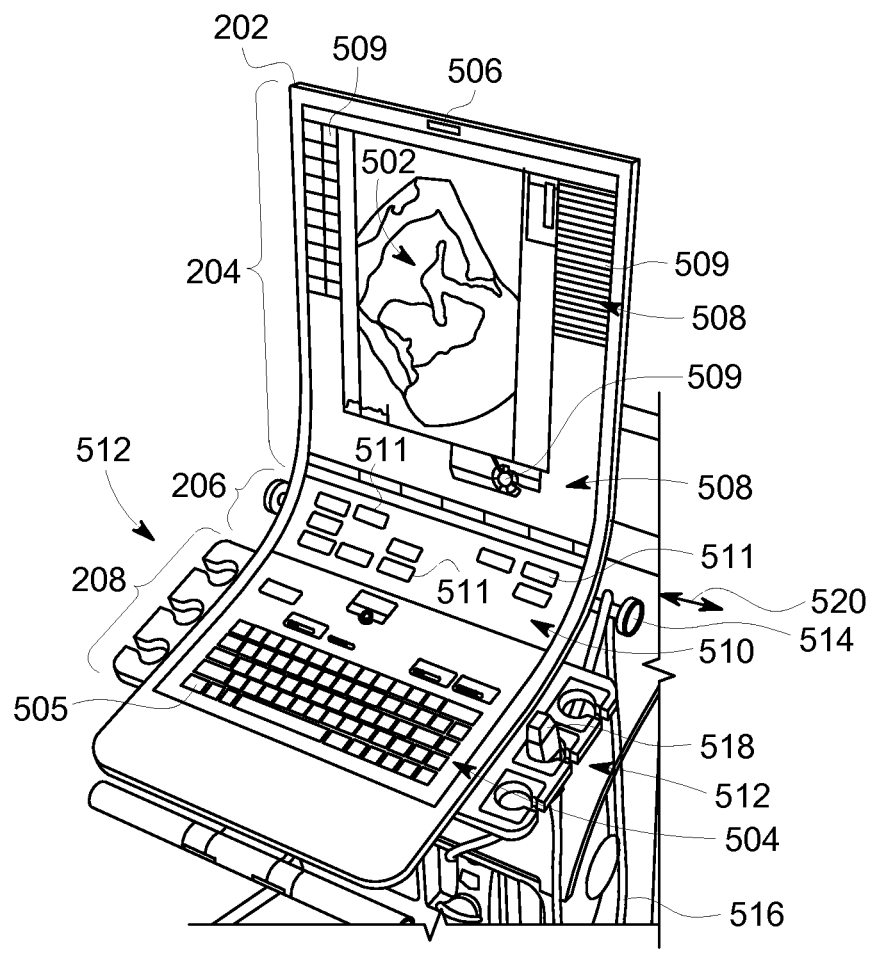
FIG. 5 illustrates a proximate view of the curved touchscreen of the ultrasound imaging system shown in FIG. 2, in accordance with an embodiment.

FIG. 5 illustrates a proximate view of the curved touchscreen 202, in accordance with an embodiment. The first interface section 204 may be configured to display one or more ultrasound images 502. Additionally or alternatively the first interface section 204 may display a graphical user interface (GUI) 508. The GUI 508 may include one or more user selectable icons 509, toolbars, pull down menus, and/or the like which may allow a user to perform editing functions, database functions, measuring functions, adjusting a view of the one or more ultrasound images (e.g., adjusting the resolution, adjusting a zoom), and/or the like. For example, the GUI 508 of the first interface section 204 may allow a user to select one or more features of a select ultrasound image (e.g., selecting from the one or more ultrasound images 502) to perform measurements, to label (e.g., insert a flag or icon) one or more features of the ultrasound image 502, perform diagnostics, and/or the like. In another example, the GUI 508 of the first interface section 204 may allow the user to perform filter functions (e.g., reduce noise) to the ultrasound image 502, crop the ultrasound image 502, reposition the ultrasound image 502 on the first interface section 204, and/or the like. In another example, the GUI 508 of the first interface section 204 may allow the user to save one or more of the ultrasound images 502 onto a remote database, onto local memory, onto remote memory, and/or the like.

In various embodiments, the curved touchscreen 202 may include an eye tracking module 904 (shown in FIG. 9). The eye tracking module 904 may include hardware, such as a processor, a controller, or other logic-based devices and/or a combination of hardware and software which is used to configure the eye tracking module 904 to adjust a vertical position of the first interface section 204 on the curved touchscreen 202 based on an eye height 602 of the user. The eye tracking module 904 may comprise and/or be communicatively coupled to an image acquisition unit 506 (e.g., a charge-coupled device (CCD) image sensor, a complementary metal-oxide-semiconductor sensor, active pixel sensor, analog image sensor, a backside illumination sensor). Optionally, the image acquisition unit 506 may be embedded within the curved touchscreen 202 as shown in FIG. 5. The image acquisition unit 506 may acquire one or more images that include data and/or pixel information corresponding to one or more features of the eye(s) of the user. For example, the one or more images may include data and/or pixel information corresponding to a pupil, a corneal reflection, the iris, the lens, and/or the like.

Figure 6:
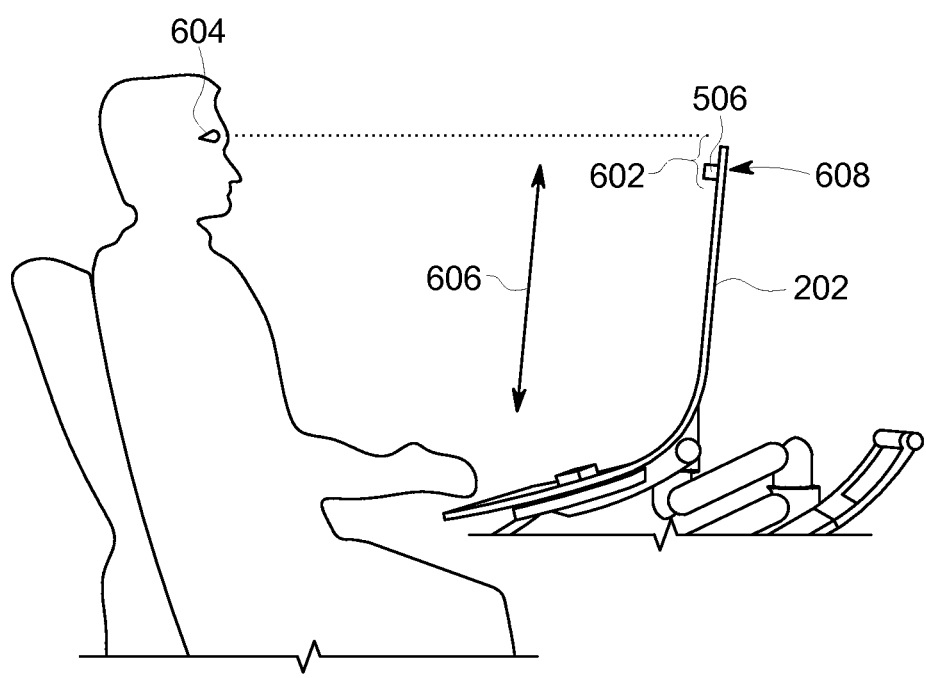
FIG. 6 illustrates a lateral perspective view of the curved touchscreen shown in FIG. 5.

Based on the one or more features of the eye, the eye tracking module 904 may be configured to determine an eye height 602 of the user. In connection with FIG. 6, the eye height 602 may correspond to a position of an eye 604 with respect to the image acquisition unit 506. FIG. 6 illustrates a lateral perspective view of the curved touchscreen 202. The image acquisition unit 506 may be at a static predetermined position with respect to the curved touchscreen 202, such as at an upper portion 608 of the curved touchscreen 202, allowing data and/or pixel information of the one or more images to correspond to approximately the same location. It should be noted that in various other embodiments, the image acquisition unit 506 may be positioned at various other locations such as on a side of the curved touchscreen 202, remotely from the curve touchscreen display 202 (e.g., positioned on the movable cart 214), or the like. Based on a location of the eye 604 in the one or more images, the eye tracking module 904 may determine the eye height 602 corresponding to a vertical position of the eye 604 with respect to the curved touchscreen 202.

The eye tracking module 904 may adjust a position of the first interface section 204 based on the eye height 604. In at least one embodiment, the eye tracking module 904 may adjust a vertical position of the first interface section 204 along an arrow 606 based on the eye height 604. For example, the eye tracking module 904 may lower or reduce the vertical position of the first interface section 204 when an eye height is below the image acquisition unit 506 relative to an eye height 602 that is above or approximately equal to a vertical position of the image acquisition unit 506. In another example, the eye tracking module 904 may increase the vertical position of the first interface section 204 when the eye height 602 is above the image acquisition unit 506 relative to an eye height that is below and/or parallel to a vertical position of the image acquisition unit 506.

Additionally or alternatively, the eye tracking module 904 may be used to interface the eye 604 of the user with the one or more user selectable icons 509 of the GUI 508. For example, the eye tracking module 904 may determine a rotation of the eye 604, for example, based on changes in corneal reflections of the eye 604. Based on the rotation of the eye 604 the eye tracking module 904 may determine a gaze location (e.g., a point of focus) of the eye 604 relative to a position on the first interface section 204. When the gaze location corresponds to a position on the first interface section 204 that is associated with a user selectable icon, the eye tracking module 904 may instruct a controller circuit 936 that the user selectable icon has been selected.

Returning to FIG. 5, the second interface section 206 may be positioned between the first interface section 204 and the third interface section 208. The second interface section 206 may display a GUI 510 with one or more user selectable icons 511 corresponding to one or more ultrasound imaging examinations, diagnostic tools, imaging modalities, and/or the like. For example, the user may select a user selectable icon corresponding to an ultrasound elasticity imaging modality.

The third interface section 208 may display a GUI 504 with one or more user selectable icons 505 corresponding to one or more acquisition settings (e.g., initiating ultrasonic pulses, adjusting a sensitivity, adjusting the ultrasonic pulses, adjusting the dynamic range) of an ultrasound probe 518 communicatively coupled to the ultrasound imaging system 200, freezing one or more ultrasound images shown on the first interface section 204, apply measurement functions (e.g., caliper), adjusting a view of the one or more ultrasound images shown on the first interface section 204 (e.g., adjusting the resolution, zooming in on areas of interest, adjusting amplification), and/or the like.

Additionally or alternatively, the one or more user selectable icons 505, 509, 511 shown on the interface sections 208, 206, 204, respectively, may be reconfigured based on a user selection from alternative interface sections 204, 206, 208. For example, the one or more user selectable icons 511 shown on the second interface section 206 may be reconfigured based from the one or more acquisition settings for the ultrasound probe 518 selected from the user selectable icons 505 on the third interface section 208.

In various embodiments, the curved touchscreen 202 may be coupled to a peripheral support structure 512. The peripheral support structure 512 may be configured to hold one or more devices that are communicatively coupled to and/or a part of the ultrasound imaging system 200. For example, the peripheral support structure 512 may be configured to hold the ultrasound probe 518.

Optionally, the curved touchscreen 202 may be coupled to a retractable hook 514 configured to hold and/or support one or more cables 516 connected to one or more devices that are communicatively coupled to and/or a part of the ultrasound imaging system 200. A position of the retractable hook 514 may be adjusted in an outward and inward position along the direction of an arrow 520. When the retractable hook 514 is in an inward position, the retractable hook 514 may be proximate to the curved touchscreen 202 such that a view of the retractable hook 514 is blocked and/or obstructed by the curved touchscreen 202. When the retractable hook 514 is in an outward position, the retractable hook 514 may be distal to the curved touchscreen 202 relative to the inward position such that a view of the retractable hook 514 is less obstructed by the curved touchscreen 22 relative to the inward position. Optionally, the retractable hook 514 may be configured to hold and/or support one or more cables 516 based on a position of the retractable hook 514. For example, when the retractable hook 514 is positioned in the outward position, the retractable hook 514 may be configured to hold and/or support the one or more cables 516. In another example, when the retractable hook 514 is positioned in the inward position, the retractable hook 514 may be configured to not hold and/or support the one or more cables 516.

Figure 7:
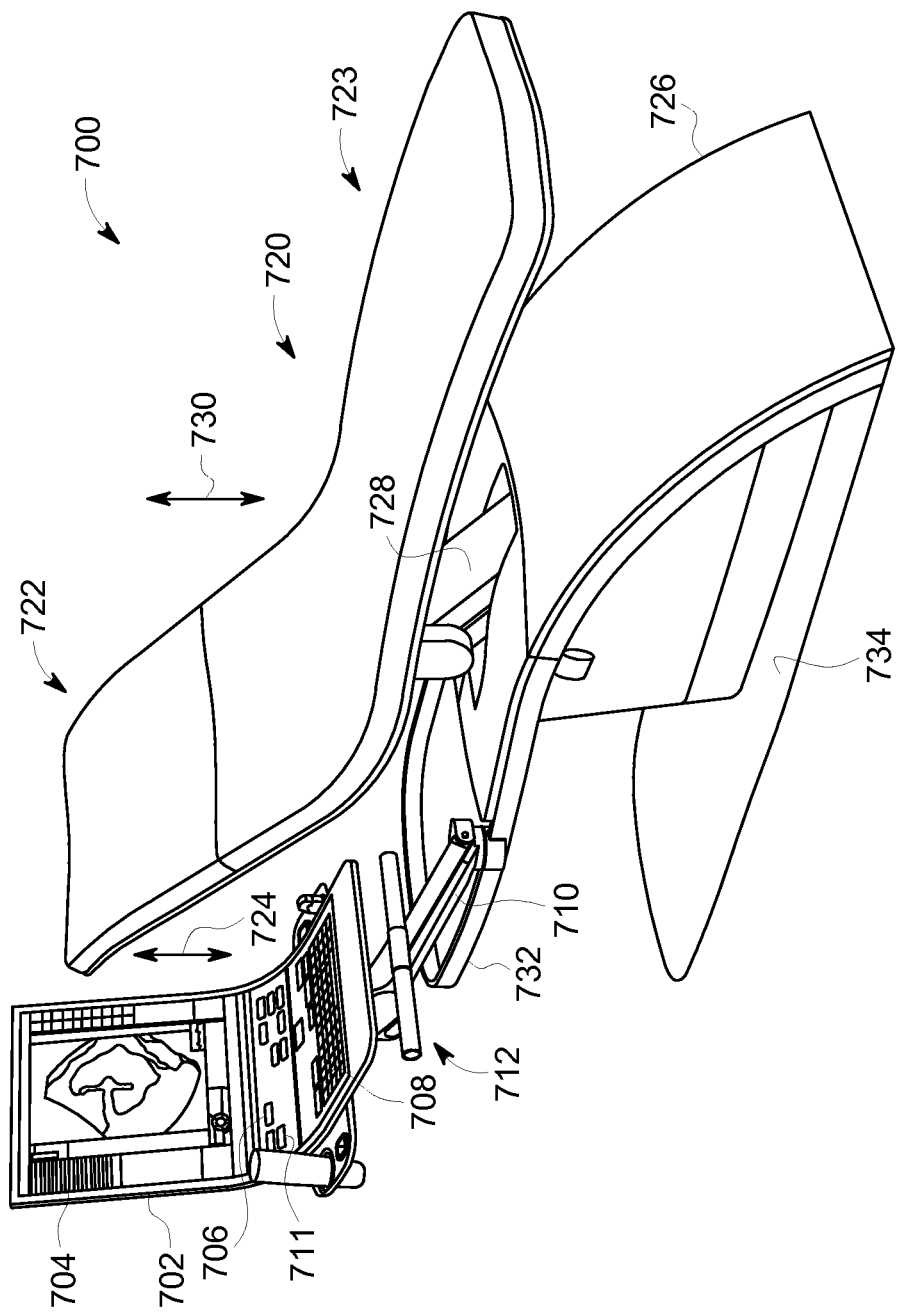
FIG. 7 illustrates a perspective view of an ultrasound imaging system, in accordance with an embodiment.

FIG. 7 illustrates a perspective view of an ultrasound imaging system 700, in accordance with one or more embodiments. The ultrasound imaging system 700 includes an examination chair 720. The examination chair 720 may be comprised of a foam or expanded rubber, such as ethylene-vinyl acetate (EVA), configured to retain an overall shape or form of one or more portions of the examination chair 720 at varying positions. The examination chair 720 includes an adjustable backrest 722. The adjustable backrest 722 may be configured to align a patient to a select position and/or posture for acquiring ultrasound images corresponding to a select ultrasound examination procedure. A technical effect of at least one embodiment includes a flexibility for the user to adapt the ultrasound imaging system 700 by adjusting a position of a patient for varying ultrasound examinations (e.g., cardiovascular examination, obstetrics examination, gynaecology examination, general ultrasound examination, abdominal examination).

For example, during a cardiovascular examination, the adjustable backrest 722 may drop or descend, traversing along an arrow 724, such that the examination chair 720 may be approximately parallel to the ground plane 734. Thereby a patient is adjusted to a lying or supine position for the cardiovascular examination. In another example, during a gynaecology examination, the adjustable backrest 722 may lift or raise, traversing along the arrow 724, such that the adjustable backrest 722 is further away from the ground plane 734 relative to the adjustable backrest 722 during cardiovascular examination. Thereby the patient is adjusted to a sitting position for the gynaecology examination. It should be noted in at least one embodiment, the examination chair 720 may include an adjustable leg rest 723 that may raise or lower corresponding to a select ultrasound examination procedure.

The examination chair 720 may be coupled to a support body 726. The support body 726 may include a base 728, which couples the examination chair 720 to the support body 726. The support body 726 may be configured to adjust a position of the base 728 thereby adjusting a vertical height of the examination chair 720 along an arrow 730. A technical effect of at least one embodiment includes better patient access to the examination chair 720. For example, when a patient is being loaded and/or unloaded onto the examination chair 720, the support body 726 may adjust a position of the examination chair 720 to a low position such that the examination chair 720 is more proximate to the ground plane 734 and/or the support body 726 relative to a position of the examination chair 720 during the select ultrasound examination procedure. Additionally or alternatively, the support body 726 may include a plurality of wheels (not shown). The plurality of wheels may be configured to allow the ultrasound imaging system 700 to be mobile. For example, the ultrasound imaging system 700 may change positions or locations within a room, be moved to an alternative room or building relative to a present location of the ultrasound imaging system 700, and/or the like.

The ultrasound imaging system 700 may include a curved touchscreen 702 which may be similar to and/or identical to the curved touchscreen 202 shown in FIG. 2. For example, the curved touchscreen 702 may include a first interface section 704, a second interface section 706, and a third interface section 708. Optionally, a position of the examination chair 720 (e.g., a position of the adjustable backrest in 722, a vertical position of the examination chair 720, a position of the leg rest 723) may be adjusted based on instructions received via the curved touchscreen 702. For example, the user may select one or more user selectable icons 711 shown on the second interface section 706 corresponding to a select ultrasound examination procedure. Based on the select ultrasound examination procedure, the curved touchscreen 702 may instruct the support body 726 to adjust a position of the adjustable backrest 722 corresponding to the select ultrasound examination procedure.

The curved touchscreen 702 may be coupled and/or mounted to an arm mount 710. The arm mount 710 may be similar to and/or identical to the arm mount 210 shown in FIG. 2. For example, the arm mount 710 may be configured to adjust a vertical position, a rotational position, and/or a tilt angle of the curved touchscreen 702. In another example, the arm mount 710 shown in FIG. 7 includes a position handle 712 which may be similar to and/or identical to the position handle 212 shown in FIG. 2.

The arm mount 710 is coupled to the examination chair 720 and the curved housing (e.g., 203) which includes the curved touchscreen 702. A position of the arm mount 710 is adjustable around the examination chair 720. For example, the arm mount 710 is coupled to the curved touchscreen 702 and a support rail 732 of the examination chair 720. The support rail 732 is positioned around a head portion (e.g., the adjustable backrest 722) of the examination chair 720. The arm mount 710 is traversable along the support rail 732. A technical effect of at least one embodiment includes allowing the user to interface and/or use the curved touchscreen 702 on one and/or both sides of the patient as well as proximate to a head of the patient.

Figure 8:
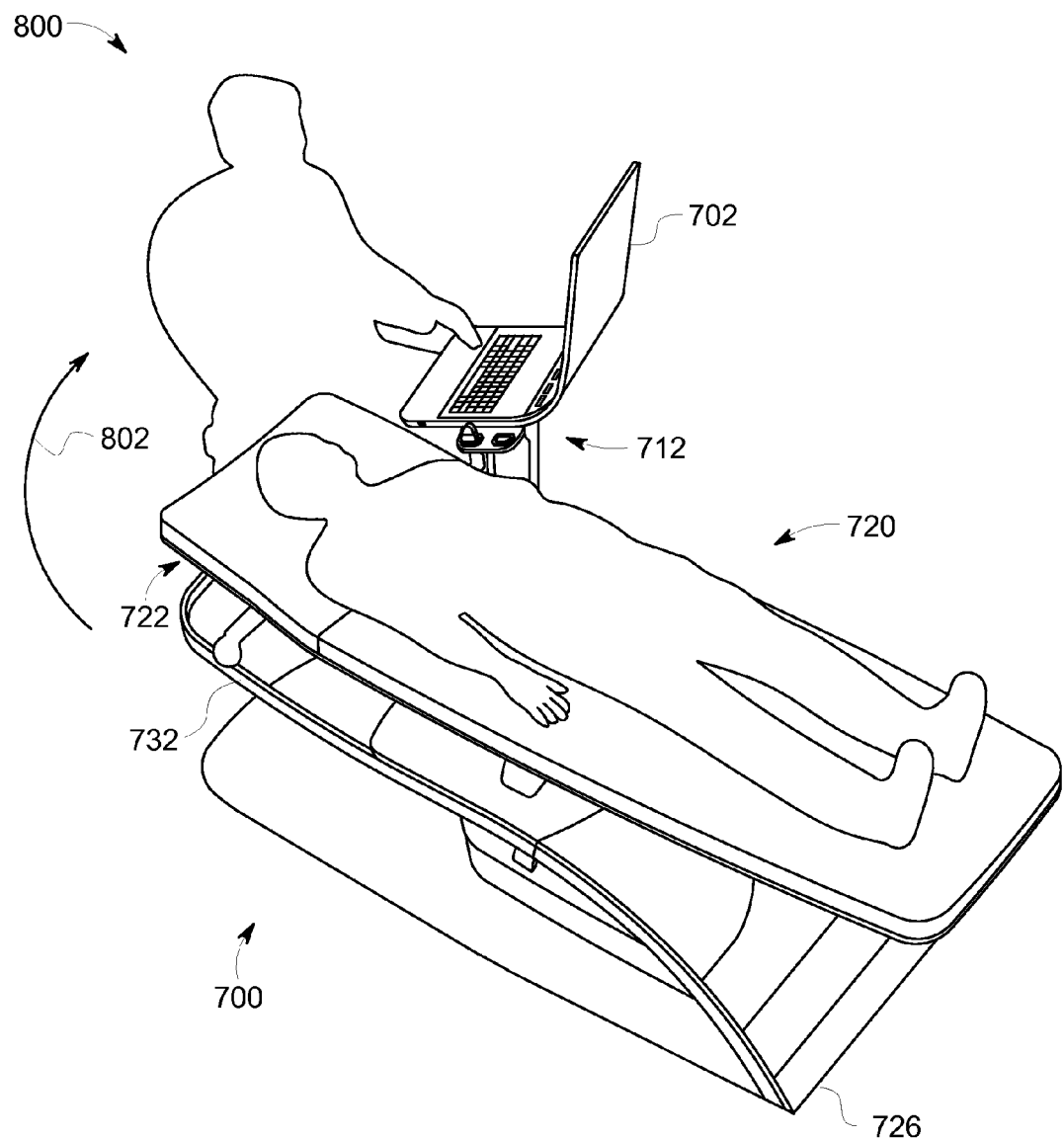
FIG. 8 illustrates an alternative view of the ultrasound imaging system shown in FIG. 7.

FIG. 8 illustrates an alternative view 800 of the ultrasound imaging system 700 having a repositioned curved touchscreen 702 relative to a position of the curved touchscreen 702 as shown in FIG. 7. For example, prior to and/or during a select ultrasound examination procedure the user may move or traverse the curved touchscreen 702 along the support rail 732 to a different position along an arrow 802. The arrow 802 follows a shape of the support rail 732. Optionally, the position handle 712 may be used by the user to adjust a position of the curved touchscreen 702 along the support rail 732. For example, the user may reposition the curved touchscreen 702 when activating a trigger (e.g., the first trigger 226, the second trigger 228) on the position handle 712.

FIG. 9 is a schematic diagram of an ultrasound imaging system 900 (e.g., the ultrasound imaging system 200, the ultrasound imaging system 700), in accordance with an embodiment. It should be noted that one or more components described in relation to the ultrasound imaging system 900 may be included within the curved touchscreen 202, 702, the movable cart 214, the support body 726, or the like. In at least one embodiment, the ultrasound imaging system 900 includes an ultrasound probe 926 having a transmitter 922 and probe/SAP electronics 910. The ultrasound probe 926 is communicatively coupled to the controller circuit 936. It should be noted that the ultrasound probe 926 may be similar and/or identical to the ultrasound probe 518 described in connection with FIG. 5. The transmitter 922 transmits a signal to a transmit beamformer 921 which in turn drives the transducer elements 924 within the transducer array 912. The transducer elements 924 emit pulsed ultrasonic signals into a patient (e.g., a body). A variety of a geometries and configurations may be used for the array 912. Further, the array 912 of transducer elements 924 may be provided as part of, for example, different types of ultrasound probes.

The transducer elements 924, for example piezoelectric crystals, emit pulsed ultrasonic signals into a body (e.g., patient) or volume. The ultrasonic signals may include, for example, one or more reference pulses, one or more pushing pulses (e.g., shear-waves), and/or one or more tracking pulses. At least a portion of the pulsed ultrasonic signals back-scatter from a region of interest (ROI) (e.g., breast tissues, liver tissues, cardiac tissues, prostate tissues, and the like) to produce echoes. The echoes are delayed in time according to a depth, and are received by the transducer elements 924 within the transducer array 912. The ultrasonic signals may be used for imaging, for generating and/or tracking shear-waves, for measuring differences in compression displacement of the tissue (e.g., strain), and/or for therapy, among other uses. For example, the probe 926 may deliver low energy pulses during imaging and tracking, medium to high energy pulses to generate shear-waves, and high energy pulses during therapy.

The transducer array 912 may have a variety of array geometries and configurations for the transducer elements 924 which may be provided as part of, for example, different types of ultrasound probes. The probe/SAP electronics 910 may be used to control the switching of the transducer elements 924. The probe/SAP electronics 910 may also be used to group the transducer elements 924 into one or more sub-apertures.

The transducer elements 924 convert the received echo signals into electrical signals which may be received by a receiver 928. The electrical signals representing the received echoes are passed through a receive beamformer 930, which performs beamforming on the received echoes and outputs a radio frequency (RF) signal. The RF signal is then provided to an RF processor 932 that processes the RF signal. Alternatively, the RF processor 932 may include a complex demodulator (not shown) that demodulates the RF signal to form IQ data pairs representative of the echo signals. The RF or IQ signal data may then be provided directly to a memory 934 for storage (e.g., temporary storage). Optionally, the output of the beamformer 930 may be passed directly to a controller circuit 936.

The ultrasound imaging system 900 also includes a processor or the controller circuit 936 to process the acquired ultrasound information (e.g., RF signal data or IQ data pairs) and prepare frames of ultrasound information for display on the display 938. The controller circuit 936 may include one or more separate processing components. For example, the controller circuit 936 may include a central processing unit (CPU), a microprocessor, a graphics processing unit (GPU), or any other electronic component capable of processing inputted data according to specific logical instructions. Having the controller circuit 936 that includes a GPU may be advantageous for computation-intensive operations, such as volume-rendering.

The controller circuit 936 is adapted to perform one or more processing operations according to a plurality of selectable ultrasound modalities on the acquired ultrasound information. Acquired ultrasound information may be processed in real-time during a scanning or therapy session as the echo signals are received. Additionally or alternatively, the ultrasound information may be stored temporarily in the memory 934 during a scanning session and processed in less than real-time in a live or off-line operation.

The ultrasound imaging system 900 may include a memory 940 for storing processed frames of acquired ultrasound information that are not scheduled to be displayed immediately or to store post-processed images (e.g., shear-wave images, strain images). The memory device 940 may include flash memory, RAM, ROM, EEPROM, or the like.

Additionally or alternatively, the memory 940 may include one or more examination chair position configurations that correspond to one or more select ultrasound examination procedures. For example, the memory 940 may include a position database. The position database may include a plurality of examination chair positions with a corresponding ultrasound examination procedure. The position database may be used by the controller circuit 936 to compare the one or more selected ultrasound examination procedures, received from a user interface 942, to one or more corresponding examination chair positions (e.g., the examination chair 720). For example, the controller circuit 936 may receive instructions to perform a cardiovascular examination from the user interface 942. The controller circuit 936 compares the received instructions with the one or more select ultrasound examination procedures stored on the position database. When the controller circuit 936 matches the received instructions with the one or more selected ultrasound examination procedures, the controller circuit 936 may output and/or instruct a position controller circuit 901 to reposition the examination chair to the corresponding position.

The position controller circuit 901 may include hardware, such as a processor, controller, or other logic-based devices and/or a combination of hardware and software which is used to control one or more electric motors to reposition one or more corresponding portions of the examination chair. For example, the position controller circuit 901 may be used to adjust a position of a base (e.g., the base 728) thereby changing a vertical height of the examination chair. In another example, the position controller circuit 901 may be used to adjust a position of an adjustable backrest (e.g., the adjustable backrest 722) thereby adjusting a patient to a lying or sitting position.

Optionally, the ultrasound imaging system 900 may include an RF interface 903. The RF interface 903 may include a receiver, a transmitter and a receiver (e.g., a transceiver), or the like. The RF interface 903 may be configured to receive information using a near field communication (NFC) protocol. Optionally, the RF interface 903 may be configured to transmit information using the NFC protocol. The NFC protocol may be a short range wireless communication protocol defined in ISO/TEC 18092/ECMA-340, ISO/IEC 21481/ECMA-352, ISO/IEC 14443, or the like. The RF interface 903 may include hardware, such as a processor, controller, or other logic-based device to detect and/or decode information of an RF signal received by an antenna (not shown). The RF signal may include information associated with and/or corresponding to a select ultrasound examination procedure. Once the RF signal is received by the RF interface 903, the RF interface 903 may output the RF signal to the controller circuit 936. The controller circuit 936 may partition select information, such as the select ultrasound examination procedure, from the RF signal and compare the partitioned information to the position database stored on memory 940.

For example, a patient and/or user may have an NFC token, NFC bracelet, or the like that transmits an RF signal corresponding to at least a select ultrasound examination procedure scheduled for the patient. The select ultrasound examination procedure may be received by the controller circuit 936 through the RF interface 903. The controller circuit 936 compares the received select ultrasound examination procedure with the one or more select ultrasound examination procedures stored on the position database.

When the controller circuit 936 matches the received ultrasound examination procedure with the one or more selected ultrasound examination procedures on the memory 940, the controller circuit 936 may output and/or instruct the position controller circuit 901 to reposition the examination chair to the corresponding position.

The position tracking circuit 948 tracks a position of the probe 926 and communicates the position to the controller circuit 936 as described above. Optionally, the controller circuit 936 may associate or correlate the ROI data acquisition location of the probe 926 with the acquisition of data corresponding to the SEI and/or SWEI, respectively, in the image memory 940.

The controller circuit 936 is connected to a curved touchscreen 902. The curved touchscreen 902 may be similar and/or identical to the curved touchscreens 202 and 702. The curved touchscreen 902 includes a user interface 942 and a display 938. The user interface 942 controls operation of the controller circuit 936 and is configured to receive inputs from the user. The user interface 942 may include a GUI (e.g., the GUI 504, 508, 510) generated by the controller circuit 936 with one or more user selectable icons, which are selected by the user. The curved touchscreen 902 may present patient information, including diagnostic and therapeutic ultrasound images to the user for review, diagnosis, analysis, and treatment. The curved touchscreen 902 may display, for example, one or more 2D, 3D, or 4D ultrasound data sets stored in the memory 934 or 940 or currently being acquired. One or both of the memory 934 and the memory 940 may store 3D data sets of the ultrasound data (e.g., shear-wave data, strain data), where such 3D data sets are accessed to present 2D and 3D images. For example, a 3D ultrasound data set may be mapped into the corresponding memory 934 or 940, as well as one or more reference planes. The processing of the data, including the data sets, may be based in part on user inputs, for example, user selections received at the user interface 942.

The controller circuit 936 is configured to analyze ultrasound signals to obtain the SEI and/or SWEI of the ROI. Furthermore, the controller circuit 936 may also automatically differentiate tissue of the ROI from non-ROI tissue. The controller circuit 936 may also be configured to receive user imaging commands for highlighting or outlining the image, a display layout (e.g., side-by-side, overlaid), or otherwise providing an overlay that indicates the ROI within the SEI and/or SWEI.

The controller circuit 936 may be configured to control the probe 926 by having the probe 926 enter into diagnostic or imaging modes such as a shear-wave mode or a strain mode based on one or more instructions received from the user interface 942. For example, the controller circuit 936 may control the probe 926 to enter the shear-wave mode. Once the probe 926 is in the shear-wave mode, the probe 926 may be controlled to deliver a pushing pulse to generate a shear-wave within the ROI automatically within a predetermined time frame or by the user using the user interface 942.

In operation, the ultrasound imaging system 900 acquires data, for example, volumetric data sets by various techniques (e.g., 3D scanning, real-time 3D imaging, volume scanning, 2D scanning with transducers having positioning sensors, freehand scanning using a voxel correlation technique, scanning using 2D or matrix array transducers, or the like). The data may be acquired by moving the probe 926, such as along a linear or curvilinear path, while scanning the ROI. At each linear or arcuate position, the probe 926 obtains scan planes that are stored in the memory 934.

The ultrasound imaging system 900 may include a shear-wave-generating circuit 923 that is operatively coupled to the controller circuit 936 or a sub-circuit of the controller circuit 936. The shear-wave generating circuit 923 is configured to control the probe 926 when the probe 926 is operated in a shear-wave mode. While in the shear-wave mode, the shear-wave generating circuit 923 may control the probe 926 to generate a shear wave at a site within the ROI of the patient. The shear-wave-generating circuit 923 may control the probe 926 or, more particularly, the transducer elements 924 to direct a shear-wave generating or pushing pulse(s) toward the predetermined site to generate the shear-wave. Alternatively, the shear-wave generating circuit 923 may control another device capable of generating shear-waves having the probe 926 measure or track the velocity as the shear-wave passes through the ROI. For example, the shear-wave-generating circuit 923 may control a therapy transducer, a mechanical actuator, or an audio device to generate the shear waves.

The ultrasound imaging system 900 also includes a strain circuit 925 that is operatively coupled to the controller circuit 936 or a sub-circuit of the controller circuit 936. The strain circuit 925 is configured to control the probe 926 when the probe 926 operated in a strain mode. While in the strain mode, the strain circuit 925 may control the probe 926 to generate a mechanical (e.g., surface vibration, freehand or step quasi-static surface displacement, or the like) or radiation force on the patient or ROI to measure the stiffness or strain of the ROI of the patient. Alternatively, the strain circuit 925 may control another device capable of generating a mechanical force on the patient or the ROI. For example, a low frequency mechanical vibrator may be applied to the skin surface and the compression motion induced in the underlying tissue, such as on the ROI, is measured by the probe 926.

Figure 10:
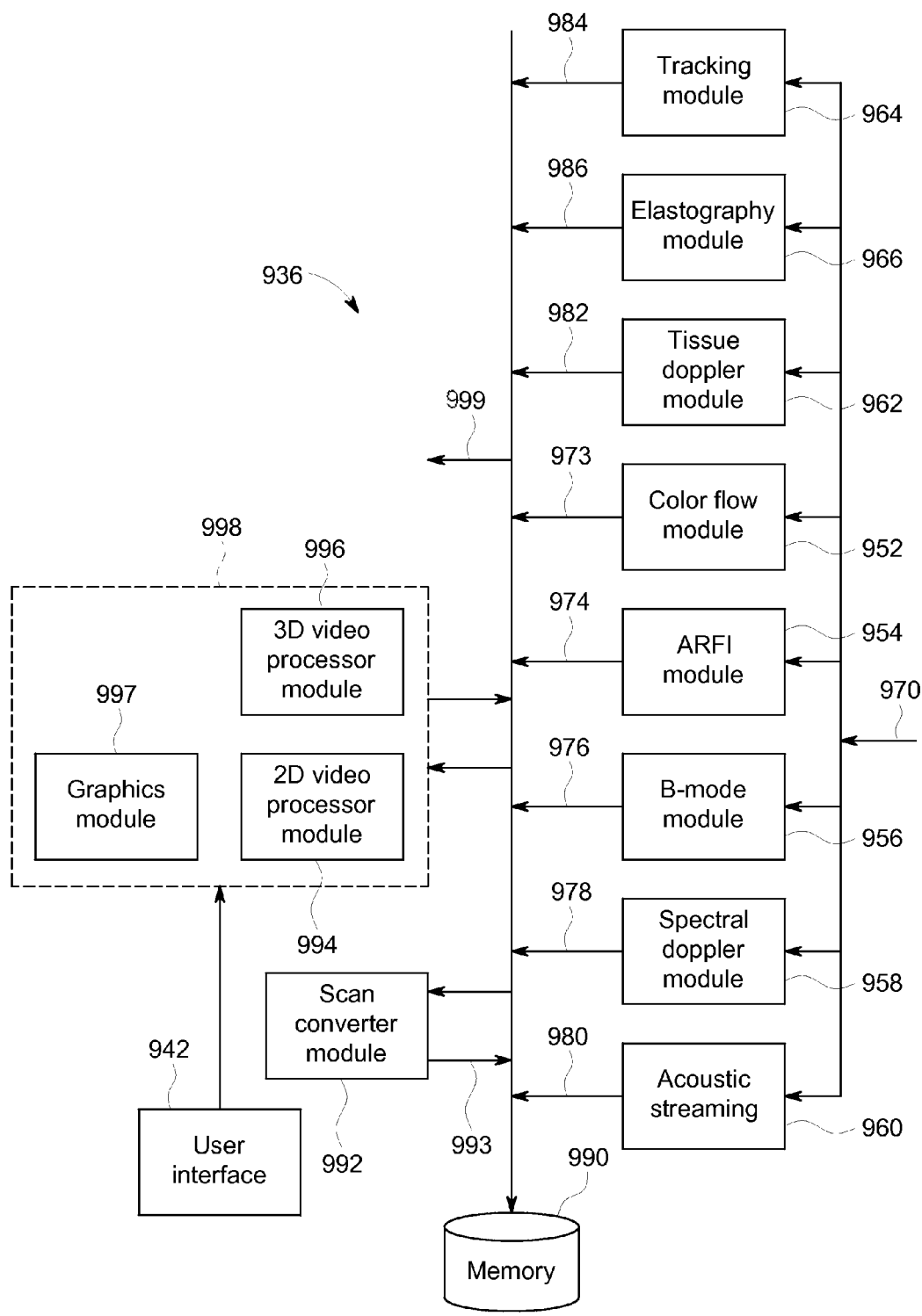
FIG. 10 is an illustration of a simplified block diagram of a controller circuit of the ultrasound imaging system of FIG. 9, in accordance with an embodiment.

FIG. 10 is an exemplary block diagram of the controller circuit 936. The controller circuit 936 is illustrated in FIG. 10 conceptually as a collection of circuits, but may be implemented utilizing any combination of dedicated hardware boards, DSPs, one or more processors, or the like. Alternatively, the circuit 936 may be implemented utilizing an off-the-shelf PC with a single processor or multiple processors, with the functional operations distributed between the processors. As a further option, the circuit 936 may be implemented utilizing a hybrid configuration in which certain modular functions are performed utilizing dedicated hardware, while the remaining modular functions are performed utilizing an off-the-shelf PC and the like. The circuit 936 also may be implemented as software circuits within a processing unit.

The circuits 952-966 perform mid-processor operations representing one or more software features of the ultrasound imaging system 900. The controller circuit 936 may receive ultrasound data 970 in one of several forms. In the embodiment of FIG. 10, the received ultrasound data 970 constitutes IQ data pairs representing the real and imaginary components associated with each data sample. The IQ data pairs are provided to one or more circuits, for example, a color-flow circuit 952, an acoustic radiation force imaging (ARFI) circuit 954, a B-mode circuit 956, a spectral Doppler circuit 958, an acoustic streaming circuit 960, a tissue Doppler circuit 962, a tracking circuit 964, and an elastography circuit 966. Other circuits may be included, such as an M-mode circuit, power Doppler circuit, among others. However, embodiments described herein are not limited to processing IQ data pairs. For example, processing may be done with RF data and/or using other methods. Furthermore, data may be processed through multiple circuits.

Each of circuits 952-966 is configured to process the IQ data pairs in a corresponding manner to generate, respectively, color-flow data 973, ARFI data 974, B-mode data 976, spectral Doppler data 978, acoustic streaming data 980, tissue Doppler data 982, tracking data 984 (e.g., ROI data acquisition location), elastography data 986 (e.g., strain data, shear-wave data), among others, all of which may be stored in a memory 990 (or memory 934 or memory 940 shown in FIG. 9) temporarily before subsequent processing. The data 973-986 may be stored, for example, as sets of vector data values, where each set defines an individual ultrasound image frame. The vector data values are generally organized based on the polar coordinate system.

A scan converter circuit 992 accesses and obtains from the memory 990 the vector data values associated with an image frame and converts the set of vector data values to Cartesian coordinates to generate an ultrasound image frame 993 formatted for display. The ultrasound image frames 993 generated by the scan converter circuit 992 may be provided back to the memory 990 for subsequent processing or may be provided to the memory 934 or the memory 940. Once the scan converter circuit 992 generates the ultrasound image frames 993 associated with the data, the image frames may be stored in the memory 990 or communicated over a bus 999 to a database (not shown), the memory 934, the memory 940, and/or to other processors (not shown).

The display circuit 998 accesses and obtains one or more of the image frames from the memory 990 or from the memory 934 and/or the memory 940 over the bus 999 to display the images onto the display 938. The display circuit 998 receives user input from the user interface 942 selecting one or image frames to be displayed that are stored on memory (e.g., the memory 990) and/or selecting a display layout or configuration for the image frames.

The display circuit 998 may include a 2D video processor circuit 994. The 2D video processor circuit 994 may be used to combine one or more of the frames generated from the different types of ultrasound information. Successive frames of images may be stored as a cine loop (4D images) in the memory 990 or memory 940. The cine loop represents a first in, first out circular image buffer to capture image data that is displayed in real-time to the user. The user may freeze the cine loop by entering a freeze command at the user interface 942.

The display circuit 998 may include a 3D processor circuit 996. The 3D processor circuit 996 may access the memory 990 to obtain spatially consecutive groups of ultrasound image frames and to generate three-dimensional image representations thereof, such as through volume rendering or surface rendering algorithms as are known. The three-dimensional images may be generated utilizing various imaging techniques, such as ray-casting, maximum intensity pixel projection and the like.

The display circuit 998 may include a graphic circuit 997. The graphic circuit 997 may access the memory 990 to obtain groups of ultrasound image frames and the ROI data acquisition locations that have been stored or that are currently being acquired. The graphic circuit 997 may generate images that include the images of the ROI and a graphical representation positioned (e.g., overlaid) onto the images of the ROI. The graphical representation may represent an outline of a treatment space, the focal point or region of the therapy beam, a path taken by the focal region within the treatment space, a probe used during the session, the ROI data acquisition location, and the like. Graphical representations may also be used to indicate the progress of the therapy session. The graphical representations may be generated using a saved graphical image or drawing (e.g., computer graphic generated drawing), or the graphical representation may be directly drawn by the user onto the image using a GUI of the user interface 942.

Figure 11:
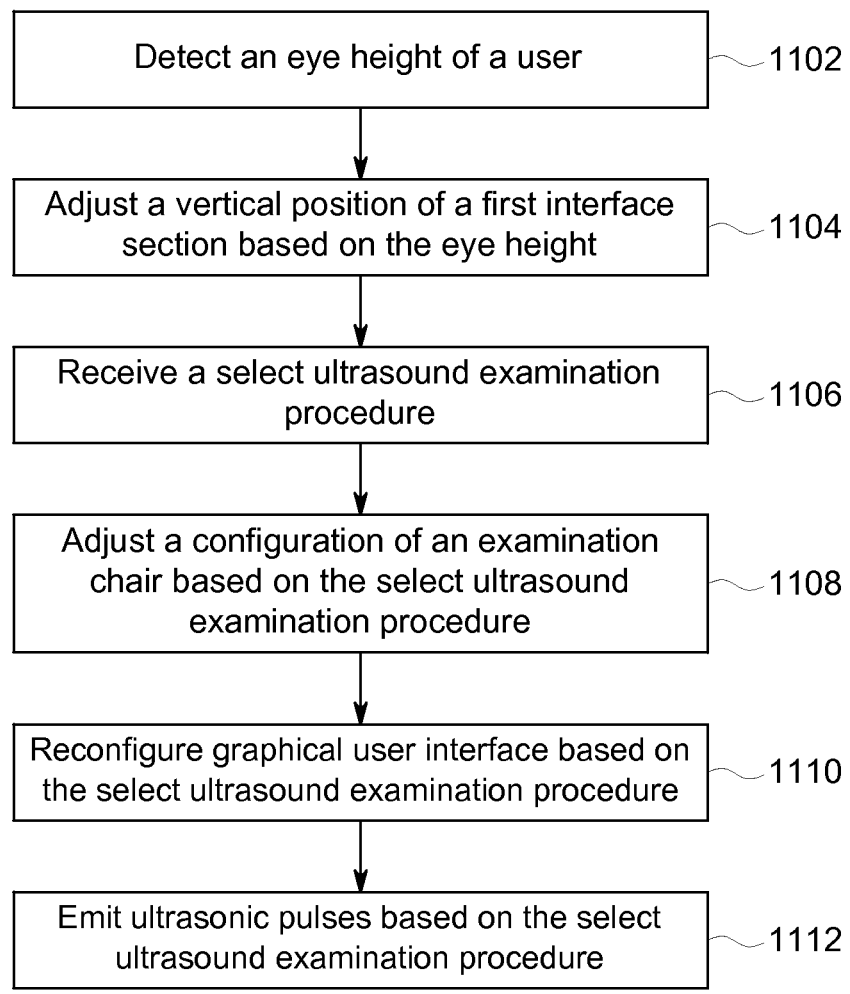
FIG. 11 is a flowchart of a method for initiating a select ultrasound examination procedure using an ultrasound imaging system, in accordance with an embodiment.

FIG. 11 illustrates a flowchart of a method 1100 for initiating a select ultrasound examination procedure using an ultrasound imaging system (e.g., the ultrasound imaging systems 200, 700, and/or 900), in accordance with various embodiments described herein. The method 1100, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 1100 may be used as one or more algorithms to direct hardware to perform one or more operations described herein. It should be noted, other methods may be used, in accordance with embodiments herein.

Beginning at 1102, an eye height 602 of the user is detected. For example, the eye tracking module 904 may be configured to determine the eye height 602 with respect to the image acquisition unit 506 based on one or more features of the eye.

At 1104 a vertical position of the first interface section 204 is adjusted based on the eye height 602.

At 1106 and select ultrasound examination procedure is received. For example, the select ultrasound examination procedure may correspond to and/or be included within an RF signal received by the RF interface 903. In another example, the select ultrasound examination procedure may be received by the curved touchscreen 202 from the user selection of one or more user selectable icons included within a GUI 504, 508, 510 (e.g., the user interface 942).

At 1108 a configuration of the examination chair 720 is adjusted corresponding to the select ultrasound examination procedure.

At 1110 a GUI (e.g., the GUI 504, 508, 510) is reconfigured based on the select ultrasound examination procedure. For example, the one or more user selectable icons 511 shown on the second interface section 206 may be reconfigured based from the one or more acquisition settings for the ultrasound probe 518 selected from the user selectable icons 505 on the third interface section 208.

At 1112 ultrasonic pulses are admitted by the ultrasound probe 518 based on the select ultrasound examination procedure.

It should be noted that the curved touchscreen 202 may be used in various embodiments other than diagnostic medical imaging. For example, the curved touchscreen 202 may be used as a display for gaming (e.g., computer games, video games, console games), automobiles, interface for automatic teller machines, general user interface displays, and/or the like It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. An ultrasound imaging system comprising:
an ultrasound probe configured to acquire ultrasound data for a region of interest;
a controller circuit communicatively coupled to the ultrasound probe configured to generate one or more ultrasound images from the ultrasound data;
a curved housing shaped to extend along a curvature angle, the curved housing includes a front panel having a curved touchscreen, wherein the curved touchscreen has at least a first interface section, a second interface section, and a third interface section formed integral with one another, wherein the first interface section and the third interface section are positioned at different display angles with respect to each other, the first interface section configured to display the one or more ultrasound images and the third interface section includes one or more user selectable icons to control the ultrasound probe.

2. The ultrasound imaging system of claim 1, wherein the curved touchscreen includes an eye tracking module comprising an image sensor configured to determine an eye height of a user, wherein the eye tracking module is configured to adjust a position of the first interface section on the curved touchscreen based on the eye height of the user.

3. The ultrasound imaging system of claim 1, further comprising an arm mount coupled to the curved housing, the arm mount configured to adjust a vertical position and a rotational position of the curved touchscreen.

4. The ultrasound imaging system of claim 3, further comprising a position handle coupled to the arm mount having a first trigger and a second trigger, wherein the vertical position of the curved touchscreen is adjustable when the first trigger is activated, and the rotational position of the curved touchscreen is adjustable when the second trigger is activated.

5. The ultrasound imaging system of claim 1, wherein the first interface section and the third interface section are positioned relative to the curved touchscreen to have biasing angles based on a visual direction of a position of an eye of the user, the biasing angles are configured to increase at least one of a contrast ratio or a luminosity.

6. The ultrasound imaging system of claim 1, wherein the curved housing is configured to be flexible such that the curvature angle formed by the curved housing is adjustable.

7. The ultrasound imaging system of claim 1, further comprising:
an examination chair; and
an arm mount coupled to the examination chair and the curved housing.

8. The ultrasound imaging system of claim 7, wherein a position of the arm mount is adjustable around the examination chair.

9. The ultrasound imaging system of claim 7, wherein the examination chair includes an adjustable backrest configured to change positions based on a select ultrasound examination procedure received from the second interface section of the curved touchscreen.

10. The ultrasound imaging system of claim 1, further comprising a retractable hook coupled to the curved touchscreen such that the retractable hook is adjustable in an outward and inward position, responsive to the retractable hook in the inward position a view of the retractable hook is obstructed by the curved touchscreen.

11. The ultrasound imaging system of claim 1, further comprising a peripheral support structure coupled to the curved housing, wherein the peripheral support structure is configured to hold the ultrasound probe.

12. The ultrasound imaging system of claim 1, wherein the curved touchscreen includes an organic light emitting diode display.

13. The ultrasound imaging system of claim 1, wherein one or more user selectable icons of the second interface section is reconfigured based on one or more acquisition settings of the ultrasound probe.

14. The ultrasound imaging system of claim 1, wherein the second interface section is positioned between the first interface section and the third interface section, wherein the third interface section includes acquisition setting such as initiating ultrasonic pulses, adjusting a sensitivity, adjusting the ultrasonic pulses, or adjusting the dynamic range of the ultrasound probe.

15. The ultrasound imaging system of claim 1, wherein the curved touchscreen includes first, second, and third displays, the first display corresponding to the first interface section, the second display corresponding to the second interface section, and the third display corresponding to the third interface section.

16. The ultrasound imaging system of claim 1, further comprising a cover-glass configured to provide a continuous glass surface area for the curved touchscreen.

17. A portable ultrasound imaging system comprising:
an ultrasound probe configured to acquire ultrasound data from a region of interest;
a controller circuit communicatively coupled to the ultrasound probe configured to generate one or more ultrasound images from the ultrasound data;
a movable cart having a plurality of wheels;
a curved housing shaped to extend along a curvature angle, the curved housing includes a front panel having a curved touchscreen, wherein the curved touchscreen has at least a first interface section, a second interface section, and a third interface section formed integral with one another, wherein the first interface section and the third interface section are positioned at different display angles with respect to each other, the first interface section configured to display one or more ultrasound images and the third interface section includes one or more user selectable icons to control the ultrasound probe; and
an arm mount coupled to the curved touchscreen and the movable cart, the arm mount configured to adjust a vertical position and a rotational position of the curved touchscreen with respect to the movable cart.

18. The portable ultrasound imaging system of claim 17, wherein the curved touchscreen includes first, second, and third displays provided within the first interface section, the second display, and the third display, respectively, and wherein the first interface section and the third interface section are positioned relative to the curved touchscreen to have different biasing angles based on a visual direction of a position of an eye of the user, the different biasing angles configured to increase at least one of a contrast ratio or a luminosity.

19. An ultrasound imaging system comprising:
an examination chair having a support rail positioned around a head portion of the examination chair;
an ultrasound probe configured to acquire ultrasound data from a region of interest;
a controller circuit communicatively coupled to the ultrasound probe configured to generate one or more ultrasound images from the ultrasound data;
a curved housing shaped to extend along a curvature angle, the curved housing includes a front panel having a curved touchscreen, wherein the curved touchscreen has at least a first interface section, a second interface section, and a third interface section formed integral with one another, wherein the first interface section and the third interface section are positioned at different display angles with respect to each other, the first interface section is configured to display one or more ultrasound images and the third interface section includes one or more user selectable icons to control the ultrasound probe; and
an arm mount coupled to the curved housing and the support rail of the examination chair, wherein the arm mount is traversable along the support rail.

20. The ultrasound imaging system of claim 19, wherein the arm mount is configured to adjust a rotational position of the curved touchscreen.

* * * * *